(12) United States Patent
Wong et al.

(10) Patent No.: US 9,637,384 B2
(45) Date of Patent: May 2, 2017

(54) FULLERENE DERIVATIVES AND THEIR APPLICATIONS IN ORGANIC PHOTOVOLTAICS

(71) Applicant: Nano and Advanced Materials Institute Limited, Hong Kong (HK)

(72) Inventors: Wing Leung Wong, Hong Kong (HK); Lai To Leung, Hong Kong (HK); Liang Zhang, Hong Kong (HK); Chi Mei Chow, Hong Kong (HK); Haojun Zhu, Hong Kong (HK); Lai Fan Lai, Hong Kong (HK); Kwok Keung Paul Ho, Hong Kong (HK)

(73) Assignee: NANO AND ADVANCED MATERIALS INSTITUTE LIMITED, Hong Kong (HK)

( * ) Notice: Subject to any disclaimer, the term of this patent is extended or adjusted under 35 U.S.C. 154(b) by 0 days.

(21) Appl. No.: 14/799,568

(22) Filed: Jul. 14, 2015

(65) Prior Publication Data

US 2016/0039676 A1 Feb. 11, 2016

Related U.S. Application Data

(60) Provisional application No. 61/999,870, filed on Aug. 8, 2014, provisional application No. 62/230,408, filed on Jun. 5, 2015.

(51) Int. Cl.
*C07F 7/08* (2006.01)
*C07F 7/18* (2006.01)
(Continued)

(52) U.S. Cl.
CPC .......... *C01B 31/0213* (2013.01); *C07C 2/86* (2013.01); *C07C 29/48* (2013.01); *C07C 67/05* (2013.01);
(Continued)

(58) Field of Classification Search
CPC ... C07F 7/0818; C07F 7/1844; C01B 31/0213
(Continued)

(56) References Cited

PUBLICATIONS

Yutaka Matsuo, "Design Concept for High-LUMO-level Fullerene Electron-acceptors for Organic Solar Cells", Chem. Lett. 2012, 41, 754759.
(Continued)

*Primary Examiner* — Porfirio Nazario Gonzalez
(74) *Attorney, Agent, or Firm* — Spruson & Ferguson (Hong Kong) Limited

(57) ABSTRACT

The present invention relates to new fullerene derivatives of formulae 1a-d, 2 and 3:

(Continued)

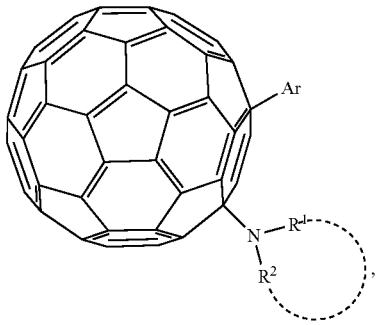

method of synthesizing said derivatives, and applications thereof in organic photovoltaics, e.g., organic solar cells. In particular, the fullerene derivatives of the present invention are soluble in non-halogenated solvents such that an environmental-friendly and low-cost fabrication method for industrialization of solar cell based on the new fullerene derivatives is provided. An ink formulation for forming a thin film on a substrate of organic photovoltaics comprising at least one of the fullerene derivatives of the present invention is also provided. Greater than 3% power conversion efficiency of the organic solar cells (area=0.16 $cm^2$) formed based on the fullerene derivatives of the present invention with less pollution and lower cost in fabrication can be achieved in the present invention.

29 Claims, 4 Drawing Sheets

(51) Int. Cl.
    C01B 31/02     (2006.01)
    H01L 51/42     (2006.01)
    C07D 295/033   (2006.01)
    C07D 207/323   (2006.01)
    C07D 209/18    (2006.01)
    H01L 51/00     (2006.01)
    C07C 2/86      (2006.01)
    C07C 29/48     (2006.01)
    C07C 67/05     (2006.01)
(52) U.S. Cl.
    CPC ....... *C07D 207/323* (2013.01); *C07D 209/18* (2013.01); *C07D 295/033* (2013.01); *C07F 7/0818* (2013.01); *C07F 7/1844* (2013.01); *H01L 51/0047* (2013.01); *H01L 51/0094* (2013.01); *H01L 51/42* (2013.01); *C07C 2104/00* (2013.01)
(58) Field of Classification Search
    USPC ........ 556/437, 482, 483, 487; 548/494, 529, 548/502; 549/4; 546/195; 252/501.1; 136/263
    See application file for complete search history.

(56) References Cited

PUBLICATIONS

Hashiguchi et al., "FeCl3-mediated Synthesis of Fullerenyl Esters as Low-LUMO Acceptors for Organic Photovoltaic Devices", Organic Letters 2012, 14, 3276-3279.
Li et al. "Functional fullerenes for organic photovoltaics", J. Mater. Chem., 2012, 22, 4161-4177.
Mi et al., "Fullerene Derivatives as Electron Acceptors for Organic Photovoltaic Cells", J. Nanosci. Nanotechnol. 2014, vol. 14, No. 2, 1064-1084.
Matsuo et al., "Columnar Structure in Bulk Heterojunction in Solution-Processable Three-Layered p-i-n. Organic Photovoltaic Devices Using Tetrabenzoporphyrin Precursor and Silylmethyl[60]fullerene", J. Am. Chem. Soc. 2009, 131, 16048-16050.
The extended European search report dated Dec. 21, 2015 issued by the European Patent Office.
Zhang et al., "Regiocontrolled Synthesis of 1,2-Di(organo)fullerenes via Copper-Assisted 1,4-Aryl Migration from Silicon to Carbon", Organic Letters 2011, 13, 6058-6061.
Matsuo et al. "Synthesis of 1,4-diaryl[60]fullerenes by bis-hydroarylation of C60 and their use in solution-processable, thin-fim organic photovoltaic cells", Tetrahedron Letters 2011, 52, 2240-2242.
Stry et al., "Novel ion-molecule reactions of fullerene dication (C602+) with ammonia", J. Am. Chem. Soc. 1992, 114, 7914-7916.
Markin et al., "Synthesis and properties of bis(biphenyl)chromium(i) 1,4-di (2-cyanoisopropyl)-1,4-dihydrofulleride and 1-(2-cyanoisopropyl)-1,2-dihydrofullerene", Russian Chemical Bulletin 2008, 57, 1970-1974.
Li et al., "Octupole-like Supramolecular Aggregates of Conical Iron Fullerene Complexes into a Three-Dimensional Liquid Crystalline Lattice", J. Am. Chem. Soc. 2010, 132, 15514-15515.
Yang et al., "Synthesis and Reactivity of 2H-Pyran Moiety in [60]Fullerene Cage Skeleton", J. Org. Chem. 2010, 75, 4567-4573.
Matsuo et al., "1-Aryl-4-Silylmethyl[60]fullerenes: Synthesis, Properties, and Photovoltaic Performance", Chem. Asian J. 2013, 8, 121-128.

FULLERENE DERIVATIVES AND THEIR APPLICATIONS IN ORGANIC PHOTOVOLTAICS

CROSS REFERENCE TO RELATED APPLICATION

Pursuant to 35 U.S.C. §119(e), this is a non-provisional patent application which claims benefits from U.S. provisional patent application Ser. No. 61/999,870 filed Aug. 8, 2014 and U.S. provisional patent application Ser. No. 62/230,408 filed Jun. 5, 2015, and the disclosures of which are incorporated herein by reference in their entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to new fullerene derivatives, method of synthesizing said derivatives, and applications thereof in organic photovoltaics, e.g., organic solar cells. In particular, the fullerene derivatives of the present invention are soluble in non-halogenated solvents such that an environmental-friendly and low-cost fabrication method for industrialization of solar cell based on the new fullerene derivatives is provided.

BACKGROUND OF THE INVENTION

Organic photovoltaic (OPV) device has become a worldwide research focus and is evaluated as one of the future key technologies for renewable energy. Over the last two decades, the solar conversion efficiency of these devices has enhanced significantly, in particular, through the development of solution-processed bulk heterojunction (BHJ) OPV cells. A lot of efforts have been devoted on the advancement of low-band gap donor materials. In contrast, there are far fewer high performance organic n-type acceptors materials reported for BHJ devices. Although many different types of donor polymers have been demonstrated with device efficiencies greater than 3%, these are limited to one or two acceptors based on the conventional C60 or C70 fullerene derivatives, such as PCBM, bis-PCBM, and ICBA.

SUMMARY OF THE INVENTION

To solve the existing problem, molecular design of sidechains attached to C60 is one of the potential pathways to tune the energy levels and by suitable modifications that can preserve good charge transport or mobility, morphology, and solubility while greater than 3% power conversion efficiency of the organic solar cells based on these newly designed fullerene derivatives with less pollution and lower cost in fabrication can be achieved.

Accordingly, in the first aspect of the present invention, one type of new fullerene derivatives is provided. These new fullerene derivatives are soluble in non-halogenated solvents such that an environmental-friendly fabrication for industrialization of solar cell can be achieved. The fabrication thereof is no less than 0.5 gram of product per batch. The material cost is also comparatively lower than the conventional fullerenes in the market. The new fullerene derivatives of the present invention are represented by the following formulae 1a-d, 2 and 3:

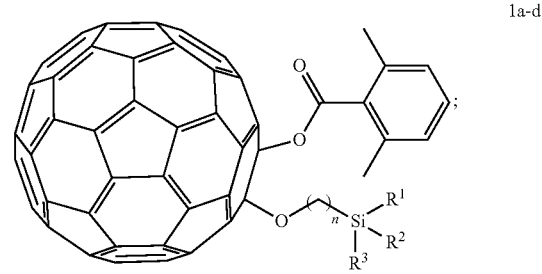

1a-d

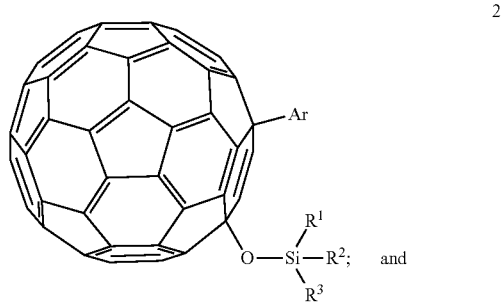

2 and

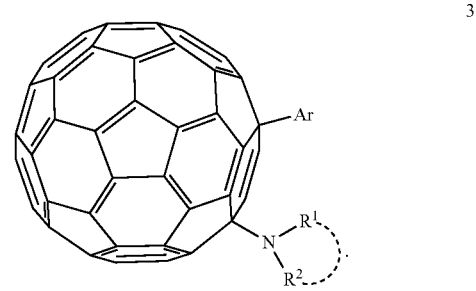

3

In one embodiment, the compounds of formulae 1a-d generally represent four different siloxyl fullerenyl esters of the present invention, respectively, which are synthesized based on a series of reactions between the fullerene, C60, and corresponding silyl chloride reagent, where $R^1$ $R^2$ and $R^3$ are independently selected from the group consisting of hydrogen, alkyl group, substituted alkyl group, alkoxy group, and substituted alkoxy group; n can be 0 or 1. Preferably, the compounds of formulae 1a, 1b, 1c, and 1d are as follows:

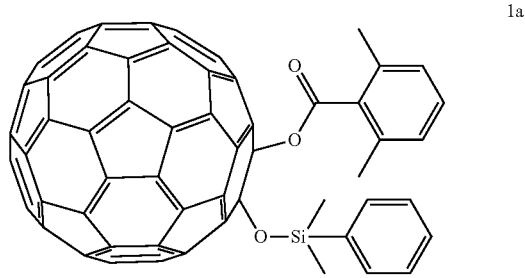 [SMILES: Cc1cccc(C)c1C(=O)OC1c2c3ccc4c5ccc6c7ccc8c9ccc%10c(c%11c2c2c3c4c3c5c6c4c7c8c5c9c%10c%11c6c2c3c4c56)C1O[Si](C)(C)c1ccccc1]

1a

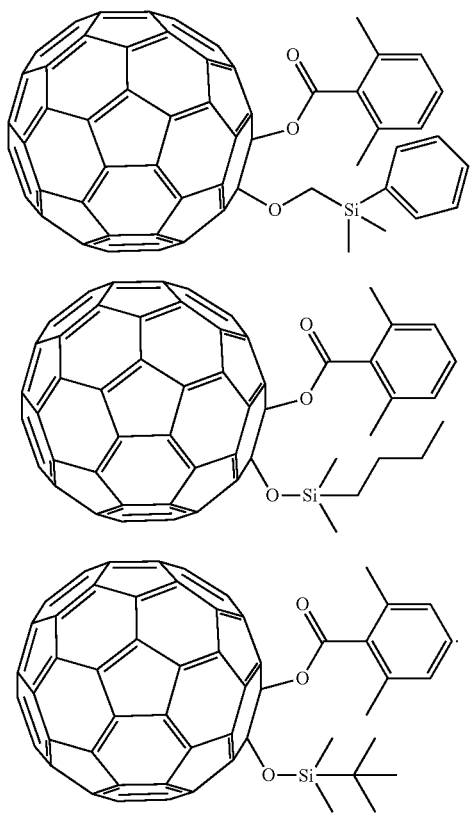

In another embodiment, Ar in the compound of formula 2 can be a simple or substituted aryl group; $R^1$ $R^2$ and $R^3$ in the compound of formula 2 are independently selected from the group consisting of hydrogen, alkyl group, substituted alkyl group, alkoxy group, and substituted alkoxy group. Preferably, the compound of formula 2, after substitution according to this embodiment, can become the compounds of formulae 2a and 2b as follows:

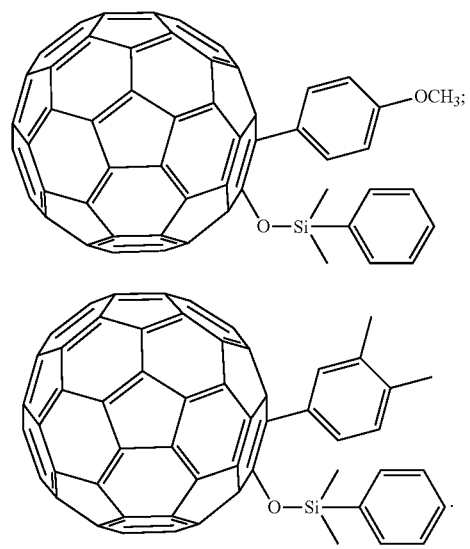

In other embodiment, Ar in the compound of formula 3 can be a simple or substituted aryl group; $R^1$ and $R^2$ in the compound of formula 3 are independently selected from the group consisting of hydrogen, alkyl group, substituted alkyl group, alkoxy group, and substituted alkoxy group of which $R^1$ and $R^2$ can also be a cyclic group of any of the above.

The second aspect of the present invention relates to a composition comprising at least one of the compounds of formulae 1a-d, 2, and/or 3 in the first aspect which is/are admixed with one or more solvents, or a mixture of said solvents. In one embodiment, said one or more solvents comprise acetone, acetonitrile, tetrahydrofuran, ethyl acetate, toluene, benzene, methanol, ethanol, 1-propanol, iso-propanol, DMSO, DMF, and other non-halogenated hydrocarbon solvents.

In one embodiment, the one or more solvents used to admix with said at least one of the compounds of formulae 1a-1d, 2, and/or 3 in said composition comprise acetone, acetonitrile, tetrahydrofuran, ethyl acetate, toluene, benzene, methanol, ethanol, 1-propanol, iso-propanol, DMSO, DMF, toluene, and other non-halogenated hydrocarbon solvents.

In another embodiment, said composition can be a solution or a mixture adapted for fabricating a thin film on a substrate of an organic solar cell.

The third aspect of the present invention relates to an ink formulation for forming a thin film on a substrate of an organic solar cell, said ink formulation comprising at least one of the compounds of formulae 1a-d, 2, and/or 3 which is/are admixed with one or more solvents, or a mixture of said solvents. In one embodiment, said one or more solvents comprise acetone, acetonitrile, tetrahydrofuran, ethyl acetate, toluene, benzene, methanol, ethanol, 1-propanol, iso-propanol, DMSO, DMF, and other non-halogenated hydrocarbon solvents.

The fourth aspect of the present invention relates to an organic solar cell having an active layer formed by said ink formulation in the third aspect incorporating one of the compounds of formulae 1a-d, 2, and/or 3 as electron acceptor admixed with one or more solvents, a mixture of said solvents, and at least one compound as electron donor. In one embodiment, said one or more solvents comprise acetone, acetonitrile, tetrahydrofuran, ethyl acetate, toluene, benzene, methanol, ethanol, 1-propanol, iso-propanol, DMSO, DMF, and other non-halogenated hydrocarbon solvents. In another embodiment, said at least one compound as electron donor comprises poly(3-hexylthiophene-2,5-diyl) (P3HT), poly[N-9'-heptadecanyl-2,7-carbazole-alt-5,5-(4,7-di-2-thienyl-2',1',3'-benzothiadiazole] (PCDTBT), and poly[[4,8-bis[(2-ethylhexyBoxy]benzo[1,2-b:4,5-b']dithio-phene-2,6-diyl][3-fluoro-2-[(2-ethylhexyl)carbonyl]thieno[3,4-b]thiophenediyl]] (PTB7). In yet another embodiment, the weight ratio of the compound of formulae 1a-d to different donor in said solvent is as follows: (i) 1a:PCDTBT=32 mg:8 mg w/w in 1 mL of dichlorobenzene; (ii) 1a:P3HT=24 mg:24 mg w/w in 1 mL of dichlorobenzene; (iii) 1a:PTB7=15 mg:10 mg w/w in 1 mL of dichlorobenzene; (iv) 1c:PCDTBT=32 mg:8 mg w/w in 1 mL of dichlorobenzene. In other embodiment, the weight ratio of the compound of formula 2 to an electron donor compound in said solvent is as follows: 2a:PCDTBT=32 mg:8 mg w/w in 1 mL of dichlorobenzene.

BRIEF DESCRIPTION OF THE DRAWINGS

Embodiments of the present invention are described in more detail hereinafter with reference to the drawings, in which.

DETAILED DESCRIPTION OF PREFERRED EMBODIMENTS

In the following description, examples and/or specific embodiments are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

EXAMPLES

Example 1

Figure 1:
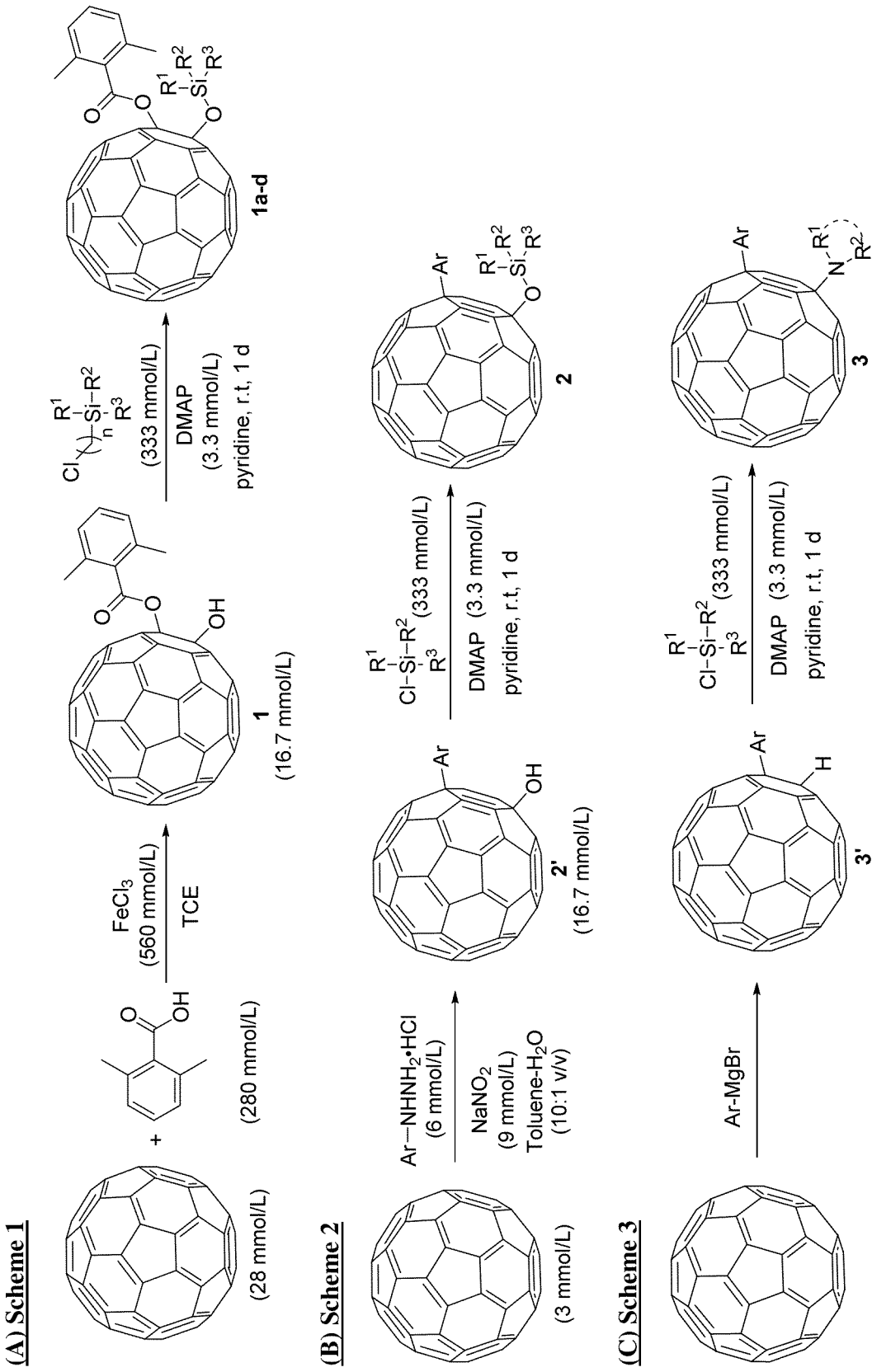
FIG. 1 is a schematic diagram showing different schemes for synthesizing different fullerene derivatives of the present invention from fullerene (C60): (A) Scheme 1 for synthesizing the compounds of formulae 1a-d; (B) Scheme 2 for synthesizing the compound of formula 2; (C) Scheme 3 for synthesizing the compound of formula 3.

In scheme 1 of FIG. 1A, the compound of formula 1 is an intermediate product formed by first reacting fullerene, C60 (2.8 mmol, 1 eq), with 2,6-dimethyl benzoic acid (28 mmol, 10 eq) in the presence of $FeCl_3$ (58 mmol, 20 eq) and 1,1,2,2-tetrachloroethane (TCE), and at room temperature (r.t.) for 5 hours. After the first reaction to form the intermediate product, the compound of formula 1 further reacts with corresponding silyl chloride reagent having the following general formula:

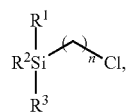

where $R^1$ $R^2$ and $R^3$ are independently selected from the group consisting of hydrogen, alkyl group, substituted alkyl group, alkoxy group, and substituted alkoxy group; n can be 0 or 1. In this example, the silyl chloride reagent comprises chlorodimethylphenylsilane, (chloromethly)dimethylphenlysilane, n-butyldimethylchlorosilane, and t-butylchlorodimethylsilane. In the presence of 4-(dimethylamino)pyridine (DMAP) (0.2 mmol, 0.2 eq) and additional pyridine (60 mL), the intermediate product, i.e. the compound of formula 1 (1.0 mmol, 1.0 eq), reacts with the corresponding silyl chloride reagent (20 mmol, 20 eq) at room temperature (r.t.) for one day to obtain the final products of scheme 1, i.e., the compounds of formulae 1a-d (general formula is shown in FIG. 1). The corresponding silyl chloride compound used to react with the compound of formula 1 to obtain the respective compound of formula 1a-d is summarized in Table 1. The final product, the compounds of formulae 1a-d, can be obtained in no less than 500 mg per batch in ~50% yield according to the reaction conditions in scheme 1.

TABLE 1

Corresponding silyl chloride reagent used to react with compound of formula 1 to obtain the compounds of formulae 1a-d:

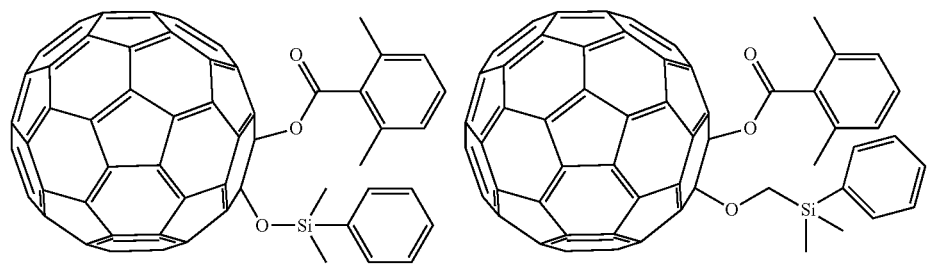

| Derivative structures | 1a | 1b |
|---|---|---|
| Silyl chloride reagent | chlorodimethylphenylsilane | (Chloromethly)dimethylphenlysilane |

TABLE 1-continued

Corresponding silyl chloride reagent used to react with compound of formula 1 to obtain the compounds of formulae 1a-d:

| Derivative structures | 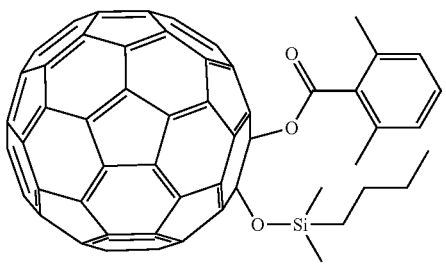 | 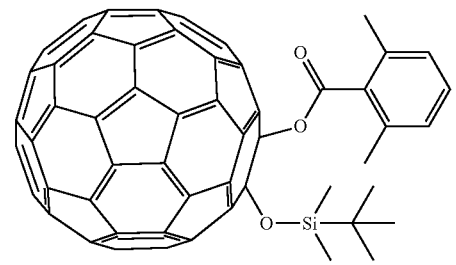 |
|---|---|---|
| | 1c | 1d |
| Silyl chloride reagent | n-butyldimethylchlorosilane | t-butylchlorodimethylsilane |

Example 2

Figure 2:
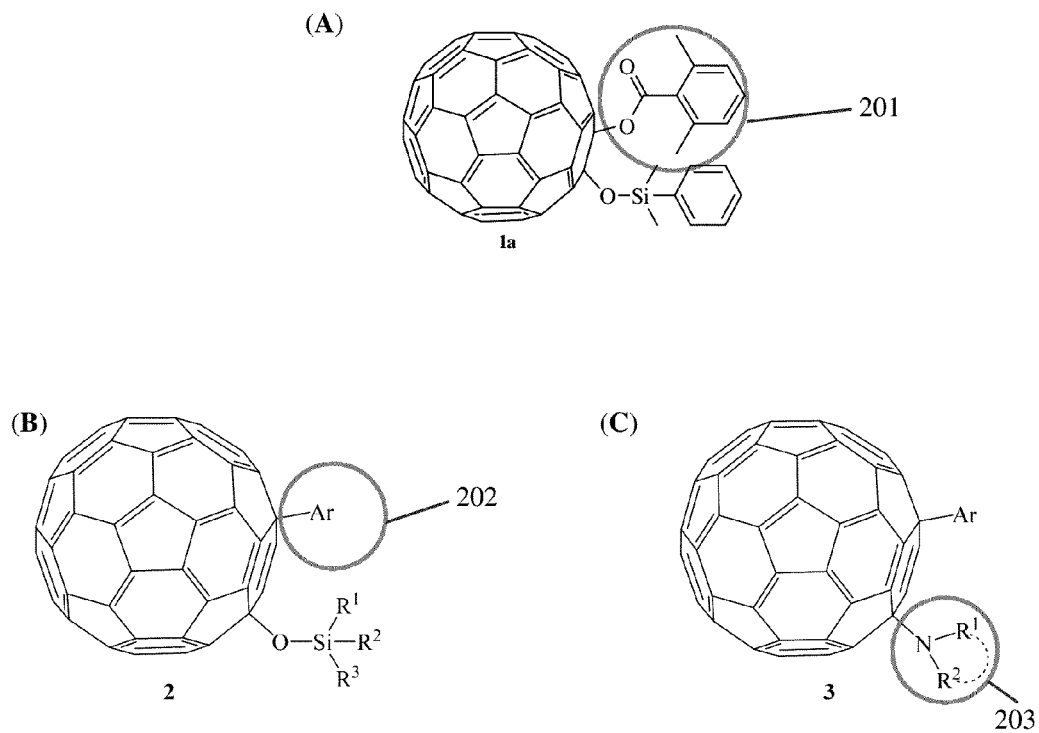
FIG. 2 is a schematic diagram showing the design of the side chain of different fullerenes of the present invention in terms of their difference in electronic properties.
Figure 2:
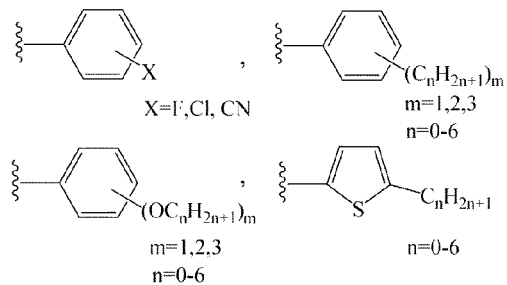
Figure 2:
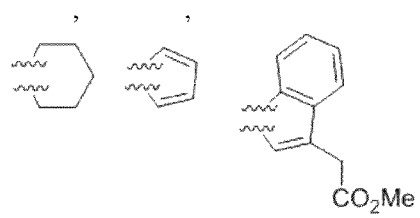

As shown in FIG. 2A, because the ester group (201) in formulae 1a-d is too electron-withdrawing, it is possible to replace the ester group by a less electron-withdrawing group, e.g., Ar group (202), as shown in FIG. 2B. Such compound in FIG. 2B is the compound of formula 2 of the present invention. In addition, siloxyl group in formula 1a or 2 can be further replaced by amine (203), which is shown in FIG. 2C. Corresponding reaction schemes for synthesizing the compounds of formulae 2 and 3 starting from fullerene, C60, are shown in FIGS. 1B and 1C, respectively.

In scheme 2 (FIG. 1B) for synthesizing the compound of formula 2 from fullerene, first of all, fullerene (1.0 mmol, 1.0 eq) reacts with $Ar-NH-NH_2 \cdot HCl$ (2.0 mmol, 2.0 eq) and $NaNO_2$ (3.0 mmol, 3.0 eq) in toluene (300 mL)-$H_2O$ (30 mL) to form the intermediate product of formula 2'. The intermediate product of formula 2' (1.0 mmol, 1.0 eq) further reacts with the silyl chloride reagent (20 mmol, 20 eq), DMAP (0.2 mmol, 0.2 eq) and additional pyridine (60 mL) at room temperature for 1 day to obtain the compound of formula 2. Ar in the compound of formula 2 can be simple or substituted aryl group; $R^1$ $R^2$ and $R^3$ in the compound of formula 2 are independently selected from the group consisting of hydrogen, alkyl group, substituted alkyl group, alkoxy group, and substituted alkoxy group. The yield of the compound of formula 2 according to scheme 2 in this example is about 23%.

In scheme 3 (FIG. 1C) for synthesizing the compound of formula 3, fullerene reacts with Ar—MgBr to form an intermediate product of formula 3'. The intermediate product of formula 3' further reacts with (ortho) 1,2-dichlorobenzene (ODCB)/dimethylformamide (DMF) and $R^1R^2NH$ or CyNH in the presence of $CuBr_2$ as a catalyst in order to obtain the compound of formula 3. Ar in the compound of formula 3 can be simple or substituted aryl group; $R^1$ and $R^2$ in the compound of formula 3 are independently selected from the group consisting of hydrogen, alkyl group, substituted alkyl group, alkoxy group, and substituted alkoxy group of which $R^1$ and $R^2$ can also be a cyclic group of any of the above.

Example 3

Figure 3:
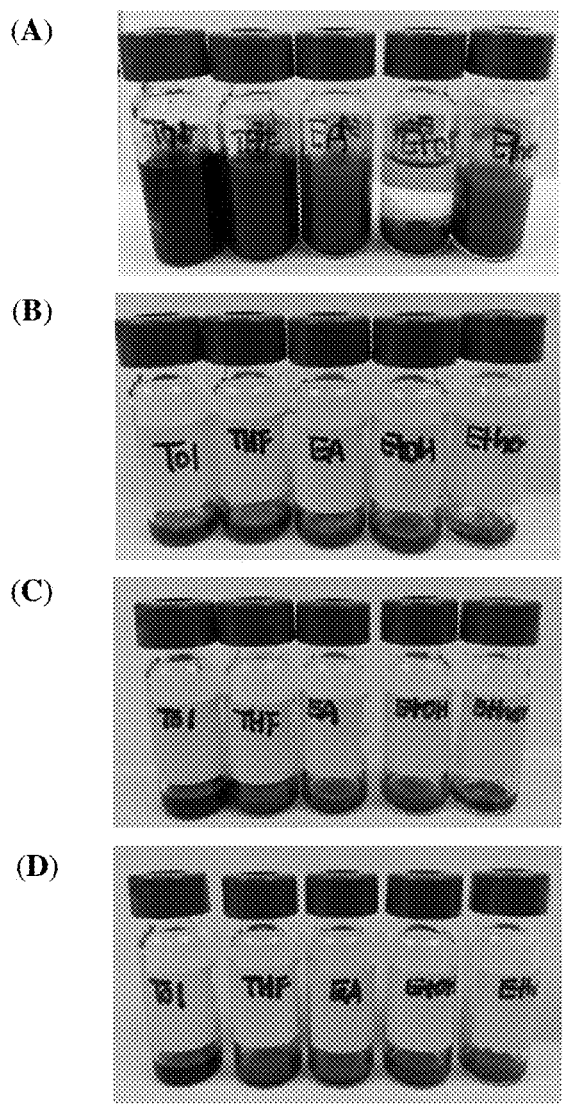
FIG. 3 are images showing the relative solubility of different compounds of (A) formula 1a, (B) formula 1b, (C) formula 1c, and (D) formula 1 d in different non-halogenated solvents; Labels on test tubes: "Tot": Toluene; "THF": Tetrahydrofuran; "EA": ethyl acetate; "EtOH": ethanol; "Ether": diethyl ether.

To demonstrate the solubility of the final products obtained from scheme 1 in non-halogenated solvent, five different organic solvents, toluene, THF, ethyl acetate, diethyl ether, and ethanol, are used to dissolve the compounds of formulae 1a-d. Each of the compounds is added into the test tubes containing five organic solvents at a concentration of 30 mg/mL. The solubility is evaluated by visual observation, and the results are shown in FIG. 3 and summarized in Table 2.

TABLE 2

Relative Solubility of Different Fullerene Derivatives in Non-halogenated Solvents:

| Different Solvent | Compound of 1a* | Compound of 1b* | Compound of 1c* | Compound of 1d* |
|---|---|---|---|---|
| Toluene | Soluble | Poorly soluble | Soluble | Slightly soluble |
| Tetrahydrofuran (THF) | Slightly soluble | Poorly soluble | Poorly soluble | Insoluble |
| Ethyl acetate | Poorly soluble | Insoluble | Insoluble | Insoluble |
| Diethyl ether | Insoluble | Insoluble | Insoluble | Insoluble |
| Ethanol | Poorly soluble | Insoluble | Insoluble | Insoluble |

*Concentration: 30 mg/mL

From FIG. 3 and Table 2, the compounds of formulae 1b and 1d are either insoluble, poorly soluble, or just slightly soluble in five solvents; compounds of formulae 1a and 1c are soluble in toluene but not in other four solvents. In general, the compound of formula 1a is relatively more soluble than 1c in the solvents in this example. It can be concluded that the compound of formula 1a is the most soluble in non-halogenated solvents used in this example among the four compounds; the compound of formula 1b is the poorest in solubility; the compound of formula 1d is the second poorest in solubility; and the compound of formula 1c is selectively soluble in non-halogenated solvents, especially good in solubility in toluene.

Example 4

Figure 4:
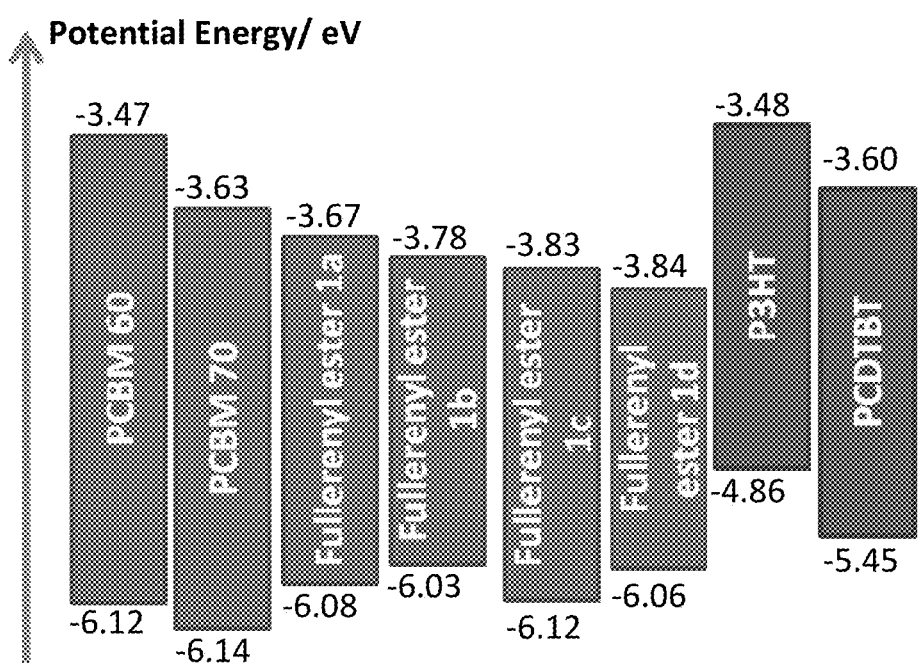
FIG. 4 is a diagram illustrating the electronic properties of different fullerene derivatives in terms of the energy difference between the Highest Occupied Molecular Orbital (HOMO) and Lowest Unoccupied Molecular Orbital (LUMO); the bar for each of the fullerene derivatives shown in this figure represents the HOMO-LUMO gap of each fullerene derivative.

To demonstrate that the compounds of the present invention has potentials to be used for forming thin film on a substrate of organic photovoltaics, the electronic properties of the present compounds are measured and compared with the conventional fullerene derivatives, PCBM 60 and PCBM 70, the different parameters are summarized in Table 3. The energy difference between HOMO and LUMO is also illustrated in FIG. 4. It is shown that the energy difference between HOMO and LUMO, or called HOMO-LUMO gap, of the compound of formula 1a is comparable to that of PCBM 60 and PCBM 70. The compounds of formulae 1b-d have similar energy difference between HOMO and LUMO, meaning their potential energy levels are similar. Among the compounds of formulae 1a-d, it appears that the compound of formula 1a has the best potential energy suitable for being applied in organic photovoltaics; the compound of formula 1c is the second best.

TABLE 3

Electrochemical properties of the fullerenyl esters (formulae 1a-1d) of the present invention compared with conventional fullerene derivatives (PCBM 60 and PCBM 70):

|  | $E_{ox}{}^a$ (eV) | HOMO$^b$ (eV) | $E_{red}{}^a$ (eV) | LUMO$^c$ (eV) | $E_g$ (eV) |
|---|---|---|---|---|---|
| PCBM 60 | 1.80 | −6.12 | −0.83 | −3.47 | 2.65 |
| PCBM 70 | 1.82 | −6.14 | −0.69 | −3.63 | 2.51 |
| Formula 1a | 1.76 | −6.08 | −0.65 | −3.67 | 2.41 |
| Formula 1b | 1.71 | −6.03 | −0.54 | −3.78 | 2.25 |
| Formula 1c | 1.80 | −6.12 | −0.49 | −3.83 | 2.29 |
| Formula 1d | 1.74 | −6.06 | −0.48 | −3.84 | 2.22 |

$^a$Onset oxidation and reduction potentials
$^b$HOMO = −e($E_{ox}$ + 4.32) (eV)
$^c$LUMO = −e($E_{red}$ + 4.32) (eV)

Example 5

According to the electrochemical properties of the compounds of formula 1a-d, the compounds of formulae 1a and 1c are selected as electron acceptor to further incorporate with P3HT, PCDTBT and PTB7 as electron donor to form an active layer of an organic solar cell structure, ITO/PEDOT/Active layer/LiF/Al (Area=0.16 cm$^2$). The open-circuit voltage (Voc), short-circuit current density (Jsc), fill factor (FF), and power conversion efficiency (PCE) of the organic solar cell having the active layer formed by different acceptor-donor pairs are summarized in Table 4.

TABLE 4

| Acceptor | Donor | Voc (V) | Jsc (mA/cm$^2$) | FF (%) | PCE (%) |
|---|---|---|---|---|---|
| PCBM 60 | P3HT | 0.57 | 9.28 | 46.8 | 2.5 |
| Compound of formula 1a | P3HT | 0.46 | 5.62 | 30.4 | 0.8 |
| PCBM 70 | PCDTBT | 0.86 | 13.13 | 40.6 | 4.6 |
| Compound of formula 1a | PCDTBT | 0.84 | 9.22 | 42.7 | 3.3 |
| Compound of formula 1c | PCDTBT | 0.76 | 8.97 | 38.2 | 2.6 |
| Compound of formula 1a | PTB7 | 0.59 | 11.7 | 34.7 | 2.4 |
| Compound of formula 2a | PCDTBT | 0.92 | 2.84 | 41.8 | 1.1 |

Cell Structure: ITO/PEDOT/Active layer/LiF/Al (Area = 0.16 cm$^2$)

From Table 4, the solar cell having the active layer formed by PCBM 70-PCDTBT pair has the highest PCE; that having the active layer formed by compound 1a-PCDTBT pair has the second highest PCE, which is higher than that of the cell having the active layer formed by PCBM 60-P3HT pair. The solar cell having the active layer formed by the compound 1c-PCDTBT pair also has a slightly higher PCE than that of the active layer formed by PCBM 60-P3HT pair. It can be concluded that the compounds of formulae 1a and 1c of the present invention can incorporate with conventional donor to form active layer of a solar cell structure with relatively higher PCE than the PCBM 60-based active layer and with similar PCE to that of the PCBM 70-based active layer. On the other hand, by replacing the electron-withdrawing ester with electron-donating arene, the LUMO of formula 2a is raised, which results in its high $V_{oc}$ in Table 4. However, the $J_{sc}$ of formula 2a is rather low presumably owing to its poor electron mobility.

The following Table 5 summarizes the differences between the present invention and the conventional fullerenes in terms of the chemical structure, synthesis method, area of active area of the organic solar cell made by fullerene derivatives as electron acceptor, power conversion efficiency, and manufacturing cost.

TABLE 5

Comparison between the fullerenes derivatives of the present invention and two conventional fullerene derivatives:

|  | Present Invention | Hashiguchi et al. (2012) | Matsuo et al. (2009) |
|---|---|---|---|
| Chemical Structure | Disubstituted with a siloxyl (OSiR3, where R = alkyl or aryl) | Disubstituted with a siloxyl (OSiR3, where R = Me only) | Methano-fullerene |
| Synthesis Method | Short (2 steps) | Short (2 steps) | Long (5 steps) |
| Area of Active Area of Organic Solar | At least 0.16 cm$^2$ | 0.04 cm$^2$ | Not available |
| Efficiency | >3% | 0.28%-1.3% | >4% |
| Cost | Below USD 110/g | Not available | USD 350/g |

INDUSTRIAL APPLICABILITY

The compounds provided in the present invention are useful as electron acceptor to form an active layer of a solar cell structure/organic photovoltaic cell which are comparable to the conventional fullerene derivatives and are environmental-friendly for industrialization because most of them are soluble in non-halogenated solvent while most conventional fullerene derivatives are only soluble in halogenated solvent, causing additional pollution to our environment.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

REFERENCES

The following references are also incorporated herein by reference in their entirety:
1. Hashiguchi, Masahiko; Obata, Naoki; Maruyama, Masashi; Yeo, Kee Sheng; Ueno, Takao; Ikebe, Tomohiko; Takahashi, Isao; Matsuo, Yutaka; *Organic Letters* 2012, 14, 3276-3279;

2. Yutaka Matsuo, Yoshiharu Sato, Takaaki Niinomi, Iwao Soga, Hideyuki Tanaka, Eiichi Nakamura, *J. AM. CHEM. SOC.* 2009, 131, 16048-16050 (existing PCBM)

What is claimed is:

1. A fullerene derivative having formula 1a-d:

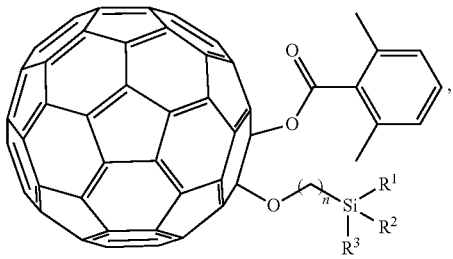

wherein $R^1$, $R^2$ and $R^3$ are independently selected from the group consisting of hydrogen, alkyl group, substituted alkyl group, alkoxy group, aryl group, and substituted alkoxy group; n is 0 or 1;
wherein when n is 0 and any two of $R^1$ $R^2$ and $R^3$ are methyl, one of $R^1$ $R^2$ and $R^3$ is selected from the group consisting of hydrogen, alkyl group having at least 2 carbons, substituted alkyl group, alkoxy group, aryl group, and substituted alkoxy group.

2. The fullerene derivative of claim 1, wherein the derivative has the following formula 1a:

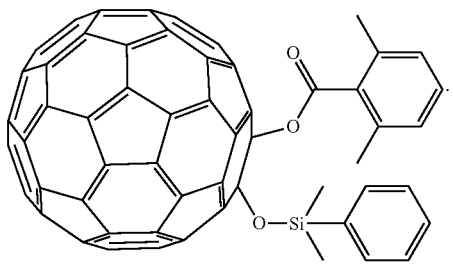

3. The fullerene derivative of claim 1, wherein the derivative has the following formula 1b:

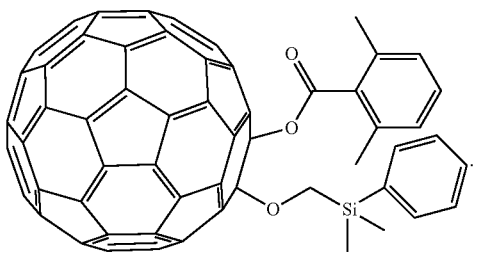

4. The fullerene derivative of claim 1, wherein the derivative has the following formula 1c:

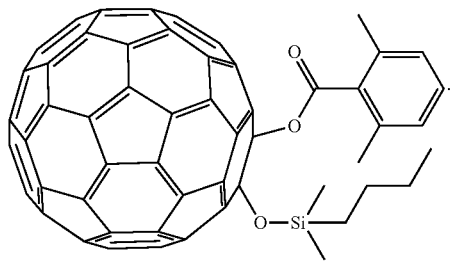

5. The fullerene derivative of claim 1, wherein the derivative has the following formula 1d:

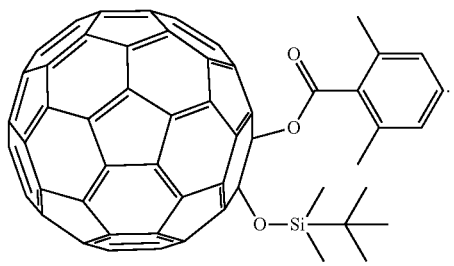

6. The fullerene derivative of claim 1, wherein n is 0, the ester group at side chain of said derivative is replaced by aryl group and $R^1$ $R^2$ and $R^3$ are independently selected from the group consisting of hydrogen, alkyl group, aryl group, substituted alkyl group, alkoxy group, and substituted alkoxy group, and the formula of said derivative having said ester group been replaced by aryl group is as follows:

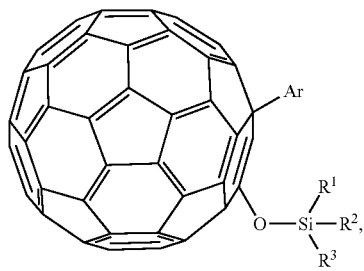

wherein Ar is a simple or substituted aryl group.

7. The fullerene derivative of claim 6, wherein said simple or substituted aryl group comprises one of the following formulae:

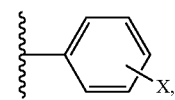

where X is F, Cl, or CN;

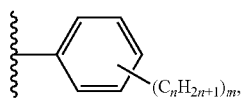

where m=1, 2, or 3; n=0 to 6;

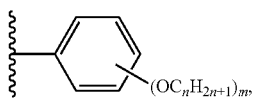

where m=1, 2, or 3; n=0 to 6; or

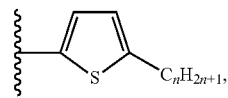

wherein n=0 to 6.

8. The fullerene derivative of claim 6, wherein said fullerene derivative comprises compounds of any of the following formulae:

2a
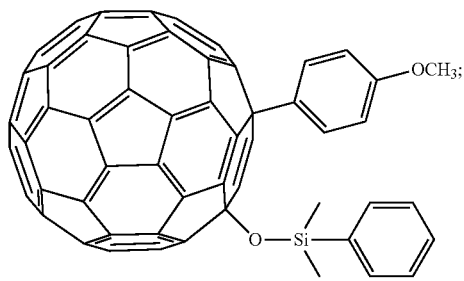

2b
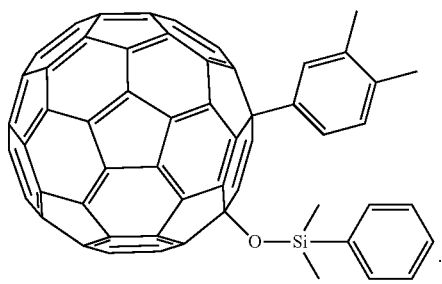

9. The fullerene derivative of claim 1, wherein the ester group and silyl group are replaced by aryl group and amine group, respectively, and the formula of said derivative having the ester group and silyl group replaced by aryl group and amine group, respectively, is as follows:

3
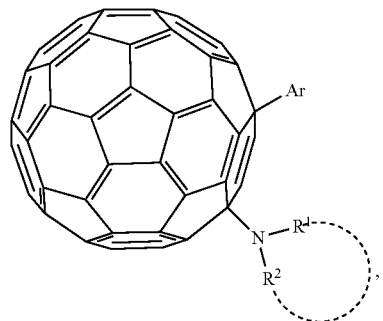

wherein Ar is a simple or substituted aryl group; $R^1$ and $R^2$ are independently selected from the group consisting of hydrogen, alkyl group, substituted alkyl group, alkoxy group, substituted alkoxy group, and cyclic group thereof.

10. The fullerene derivative of claim 9, wherein said cyclic group for $R^1$ and $R^2$ comprises one of the following formulae:

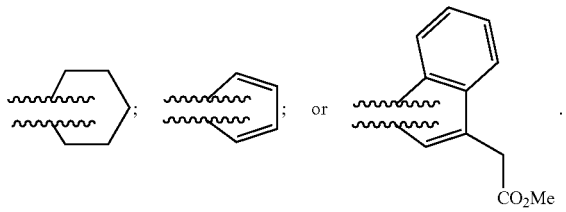 [SMILES: *CCCCC* ; */C=C\C=C/* ; */C=C(/CC(=O)OC)c1ccccc1*]

11. A method of synthesizing the fullerene derivative of claim 1, said method comprising:
  a) reacting fullerene (2.8 mmol) with 2,6-dimethyl benzoic acid (28 mmol) in the presence of $FeCl_3$ (56 mmol) and 1,1,2,2-tetrachloroethane (100 mL) (TCE), and at room temperature (r.t.) for 5 hours to obtain an intermediate product of formula 1:

1
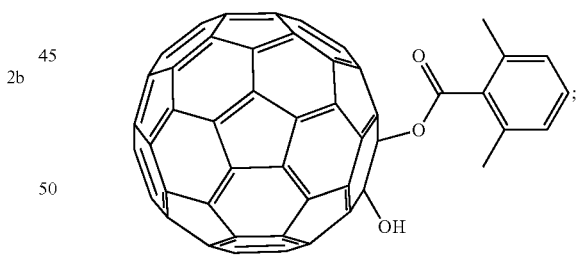

b) reacting said intermediate product of formula 1 (1.0 mmol) with a corresponding silyl chloride reagent (20 mmol) having the following general formula:

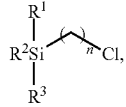

in the presence of 4-(dimethylamino)pyridine (0.2 mmol) and additional pyridine (60 mL) at room temperature (r.t.) for one day to obtain the compound of formulae 1a-d:

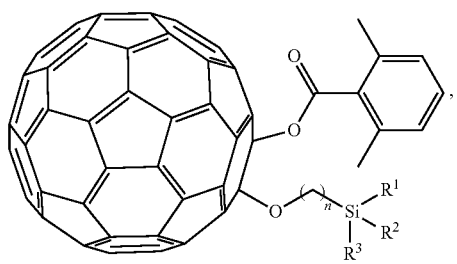

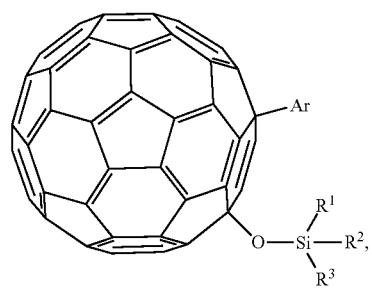

wherein $R^1$ $R^2$ and $R^3$ are independently selected from the group consisting of hydrogen, alkyl group, substituted alkyl group, alkoxy group, aryl group, and substituted alkoxy group; n is 0 or 1;

wherein when n is 0 and any two of $R^1$ $R^2$ and $R^3$ are methyl, one of $R^1$ $R^2$ and $R^3$ is selected from the group consisting of hydrogen, alkyl group having at least 2 carbons, substituted alkyl group, alkoxy group, aryl group, and substituted alkoxy group.

12. The method of claim 11, wherein said silyl chloride reagent comprises chlorodimethylphenylsilane, (chloromethly)dimethylphenlysilane, n-butyldimethylchlorosilane, and t-butylchlorodimethylsilane.

13. The method of claim 11, wherein the compounds of formulae 1a-d are obtained in no less than 500 mg per batch in about 50% yield.

14. A method of synthesizing the fullerene derivative of claim 6, said method comprising:

a) reacting fullerene (1.0 mmol) with Ar—NH—NH$_2$.HCl (2.0 mmol) and NaNO$_2$ (3.0 mmol) in toluene (300 mL)-H$_2$O (30 mL) to form an intermediate product of formula 2':

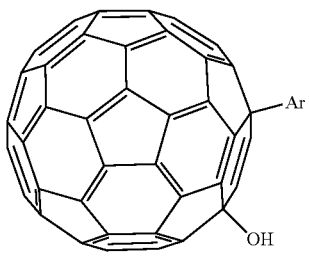

b) reacting said intermediate product of formula 2' (1.0 mmol) with a silyl chloride reagent (20 mmol) having the following formula:

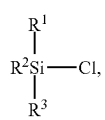

in the presence of 4-(dimethylamino)pyridine (0.2 mmol) and additional pyridine (60 mL) at room temperature for 1 day to obtain the compound of formula 2:

wherein Ar is a simple or substituted aryl group or substituted thienyl group; $R^1$ $R^2$ and $R^3$ are independently selected from the group consisting of hydrogen, alkyl group, aryl group, substituted alkyl group, alkoxy group, and substituted alkoxy group.

15. The method of claim 14, wherein said simple or substituted aryl group or substituted thienyl group comprises one of the following formulae:

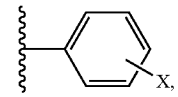

where X is F, Cl, or CN;

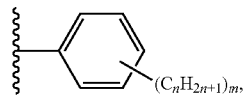

where m=1, 2, or 3; n=0 to 6;

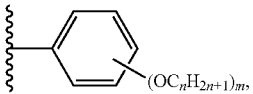

where m=1, 2, or 3; n=0 to 6; or

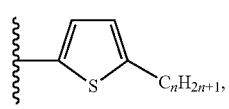

wherein n=0 to 6.

16. The method of claim 14, wherein yield of the compound of formula 2 is 23%.

17. A method of synthesizing the fullerene derivative of claim 9, said method comprising:

a) reacting fullerene with Ar—MgBr to form an intermediate product of formula 3':

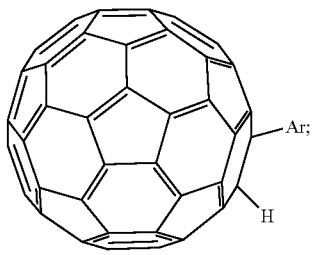

b) reacting said intermediate product of formula 3' with (ortho) 1,2-dichlorobenzene or dimethylformamide, and $R^1R^2NH$ or CyNH, in the presence of $CuBr_2$ as a catalyst in order to obtain the compound of formula 3:

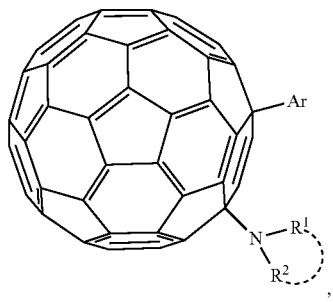

wherein Ar is a simple or substituted aryl group; $R^1$ and $R^2$ are independently selected from the group consisting of hydrogen, alkyl group, substituted alkyl group, alkoxy group, substituted alkoxy group, and cyclic group thereof.

18. The method of claim 17, wherein said cyclic group for $R^1$ and $R^2$ comprises one of the following formulae:

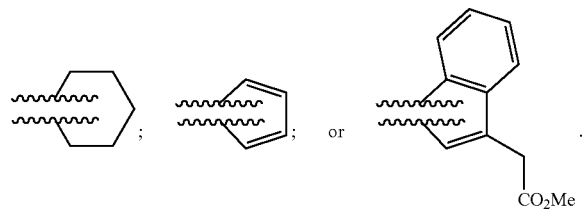 [SMILES: *CCCCC* ; */C=C\C=C/* ; */C=C(/CC(=O)OC)c1ccccc1*]

19. An ink formulation for forming a thin film on a substrate of organic photovoltaics comprising the compound of formulae 1a-d according to claim 1 admixed with one or more solvents, or a mixture of said solvents, wherein weight ratio of the compound of formulae 1a-d to an electron donor compound in said solvent ranges from 15-32: 8-20 w/w in 1 mL of said solvent.

20. The ink formulation of claim 19, wherein said solvents comprise acetone, acetonitrile, tetrahydrofuran, ethyl acetate, toluene, benzene, methanol, ethanol, 1-propanol, iso-propanol, DMSO, DMF, and other non-halogenated hydrocarbon solvents.

21. An ink formulation for forming a thin film on a substrate of organic photovoltaics comprising the compound of formula 2 according to claim 6 admixed with one or more solvents, or a mixture of said solvents, wherein weight ratio of the compound of formula 2 to an electron donor compound in said solvent is 32:8 w/w in 1 mL of said solvent.

22. The ink formulation of claim 21, wherein said solvents comprise acetone, acetonitrile, tetrahydrofuran, ethyl acetate, toluene, benzene, methanol, ethanol, 1-propanol, iso-propanol, DMSO, DMF, and other non-halogenated hydrocarbon solvents.

23. An ink formulation for forming a thin film on a substrate of organic photovoltaics comprising the compound of formula 3 according to claim 9 admixed with one or more solvents, or a mixture of said solvents.

24. The ink formulation of claim 23, wherein said solvents comprise acetone, acetonitrile, tetrahydrofuran, ethyl acetate, toluene, benzene, methanol, ethanol, 1-propanol, iso-propanol, DMSO, DMF, and other non-halogenated hydrocarbon solvents.

25. An active layer of an organic solar cell formed by the ink formulation of claim 19.

26. An active layer of an organic solar cell formed by the ink formulation of claim 21.

27. An active layer of an organic solar cell formed by the ink formulation of claim 23.

28. The active layer of claim 25, wherein said active layer has an area of at least 0.16 cm$^2$ and power conversion efficiency of greater than 3%.

29. The active layer of claim 26, wherein said active layer has an area of at least 0.16 cm$^2$ and power conversion efficiency of greater than 3%.

* * * * *